(12) United States Patent
Yamazaki

(10) Patent No.: US 8,922,770 B2
(45) Date of Patent: Dec. 30, 2014

(54) SPECTRAL DEVICE AND CONFOCAL SCANNING MICROSCOPE PROVIDED WITH SPECTRAL DEVICE

(71) Applicant: Olympus Corporation, Shibuya-ku, Tokyo (JP)

(72) Inventor: Kentaro Yamazaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/893,184

(22) Filed: May 13, 2013

(65) Prior Publication Data

US 2013/0308129 A1 Nov. 21, 2013

(30) Foreign Application Priority Data

May 18, 2012 (JP) .................................. 2012-114953

(51) Int. Cl.
*G01J 3/28* (2006.01)
*G01N 21/25* (2006.01)
*G02B 21/00* (2006.01)
*G01N 21/64* (2006.01)
*G01J 3/02* (2006.01)
*G01J 3/18* (2006.01)
*G01J 3/44* (2006.01)

(52) U.S. Cl.
CPC .......... *G01N 21/255* (2013.01); *G02B 21/0076* (2013.01); *G01N 21/6458* (2013.01); *G01J 3/021* (2013.01); *G01J 3/1804* (2013.01); *G01J 3/4406* (2013.01); *G01J 3/0208* (2013.01)
USPC ......................................... 356/328

(58) Field of Classification Search
CPC ............. G01J 3/02; G01J 3/18; G01J 3/2803; G01J 3/2823; G01J 3/28
USPC .......................................... 356/328
See application file for complete search history.

(56) References Cited

U.S. PATENT DOCUMENTS

2007/0242268 A1 10/2007 Dobschal et al.

FOREIGN PATENT DOCUMENTS

JP 2007-286043 A 11/2007
JP 2011-232032 A 11/2011

*Primary Examiner* — Tarifur Chowdhury
*Assistant Examiner* — Md Rahman
(74) *Attorney, Agent, or Firm* — Holtz, Holtz, Goodman & Chick PC

(57) ABSTRACT

Spectral device includes: diffraction element which disperses light for each wavelength; optical condensing system which condenses diffracted light of specific order generated by diffraction in the diffraction element; photo-detector arranged at position where the diffracted light of the specific order is condensed by the optical condensing system; first deflection device which inverts the direction of travel of second light as zeroth-order diffracted light generated by diffraction of first light which has entered the diffraction element as parallel luminous flux, and leads the second light into the diffraction element; and second deflection device which deflects the diffracted light of the specific order generated by diffraction of the second light which has entered the diffraction element in the same direction as the diffracted light of the specific order generated by the diffraction of the first light, and leads the deflected light into the optical condensing system.

13 Claims, 22 Drawing Sheets

⟨PRIOR ART⟩

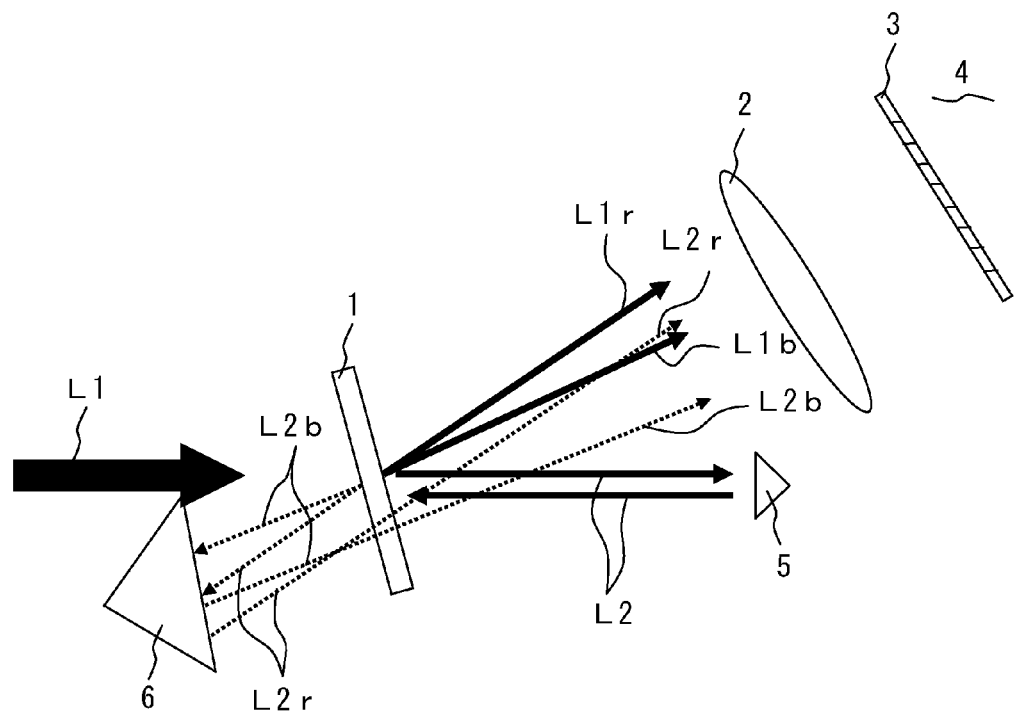
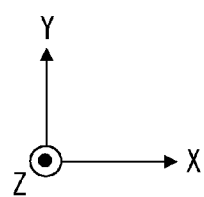
F I G. 2 A

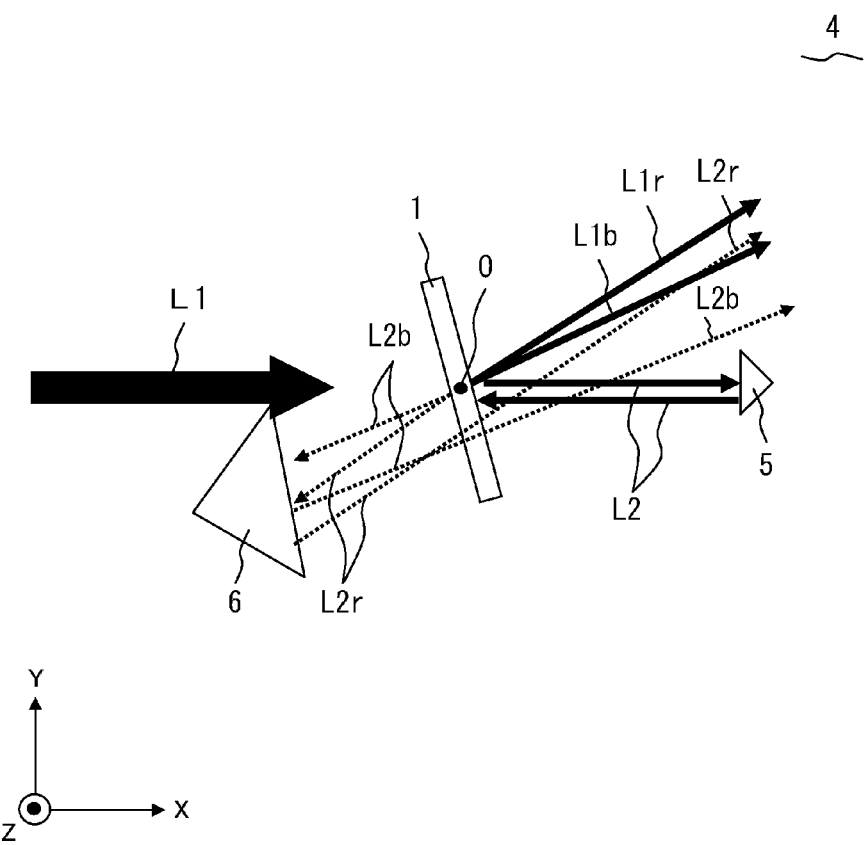
F I G. 4 A

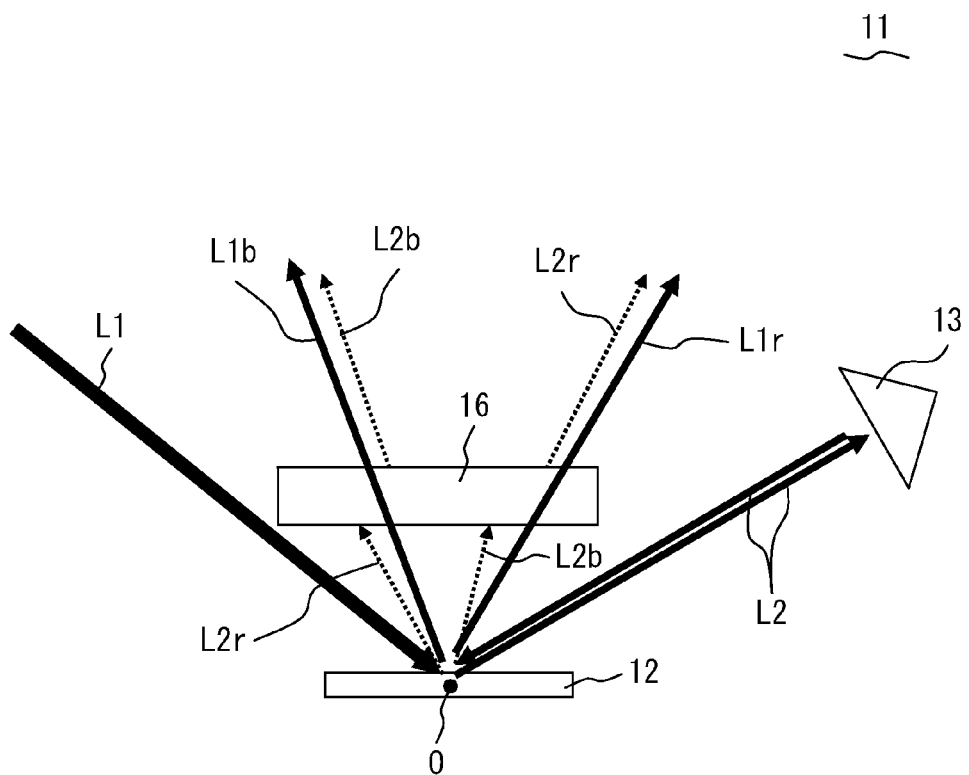
F I G. 7A

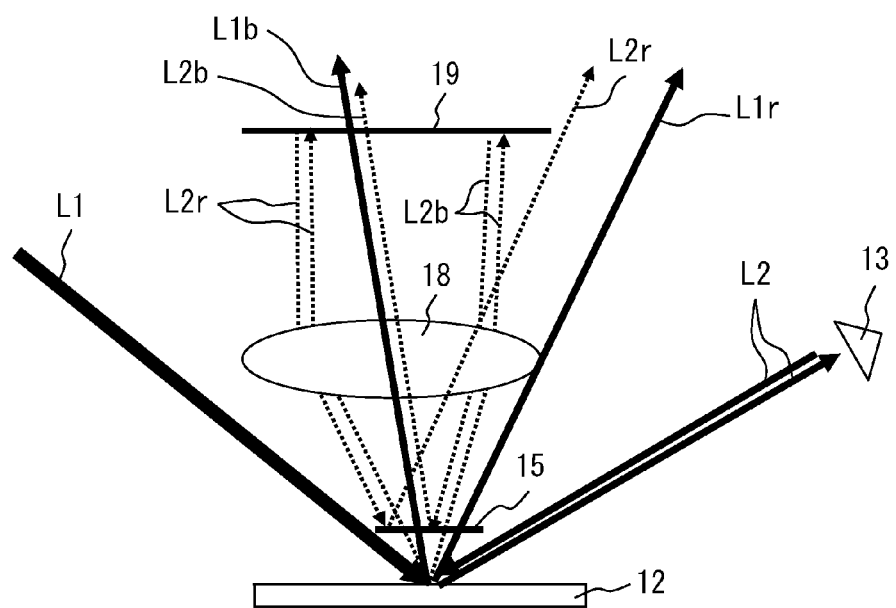
F I G. 8 A

SPECTRAL DEVICE AND CONFOCAL SCANNING MICROSCOPE PROVIDED WITH SPECTRAL DEVICE

CROSS-REFERENCE TO RELATED APPLICATIONS

This application is based upon and claims the benefit of priority from prior Japanese Patent Application No. 2012-114953, filed on May 18, 2012, the entire contents of which are incorporated herein by this reference.

BACKGROUND OF THE INVENTION

1. Field of the Invention

The present invention is related to a spectral device and a confocal scanning microscope provided with the spectral device.

2. Description of the Related Art

At present, a microscope provided with a spectral device which acquires wavelength information about light by dispersing and detecting light from a sample has become dominant in the field of a fluorescent microscope. Since the fluorescence detected by a fluorescent observation is very feeble, high detection efficiency is required for the spectral device included in a fluorescent microscope.

In a spectral device, light is generally dispersed by a diffraction grating which is designed so that the diffraction efficiency of primary diffracted light (hereafter referred to as primary diffraction efficiency) may be higher. Recently, a spectral device which realizes high detection efficiency of about 80% has been developed by adopting a diffraction grating having high primary diffraction efficiency.

In addition, from a point of view different from the improvement of a unit performance of a diffraction grating, a technique of realizing a spectral device having high detection efficiency has also been studied. For example, in the Japanese Laid-open Patent Publication No. 2007-286043, a technique of re-using zeroth-order diffracted light generated by a diffraction grating is disclosed. The spectral analysis unit disclosed by the Japanese Laid-open Patent Publication No. 2007-286043 has a configuration of circulating a zeroth-order diffracted luminous flux by leading the zeroth-order diffracted luminous flux generated by a diffraction grating to the diffraction grating with a mirror.

A diffraction grating has the characteristic of changing a peak wavelength to the diffraction efficiency which is depending on the angle of incidence. Therefore, to detect the fluorescence of a requested wavelength depending on the fluorescent substance etc. with high efficiency, it is requested that the spectral device is configured to change an angle of incidence by rotating a diffraction grating.

SUMMARY OF THE INVENTION

An aspect of the present invention provides a spectral device including: a diffraction element which disperses light for each wavelength; an optical condensing system which condenses diffracted light of a specific order generated by the diffraction in the diffraction element; a photo-detector arranged at the position where the diffracted light of the specific order is condensed by the optical condensing system; a first deflection device which inverts the direction of travel of second light as a zeroth-order diffracted light generated by the diffraction of first light which has entered the diffraction element as a parallel luminous flux, and leads the second light into the diffraction element; and a second deflection device which deflects the diffracted light of the specific order generated by the diffraction of the second light which has entered the diffraction element in the same direction as the diffracted light of the specific order generated by the diffraction of the first light, and leads the deflected light into the optical condensing system.

An aspect of the present invention is a confocal scanning microscope provided with the spectral devices described above.

BRIEF DESCRIPTION OF THE DRAWINGS

The present invention will be more apparent from the following detailed description when the accompanying drawings are referenced.

FIG. 2A is the outline of a plan view of the spectral device according to the embodiment 1;

FIG. 4A is the outline of a plan view of the spectral device according to the embodiment 1 before the rotation of a diffraction element;

FIG. 7A is the outline of a plan view of the spectral device according to the embodiment 3 before rotating the diffraction element;

FIG. 8A is the outline of a plan view of the spectral device according to the embodiment 4;

DESCRIPTION OF THE EMBODIMENTS

Embodiment 1

Figure 1:
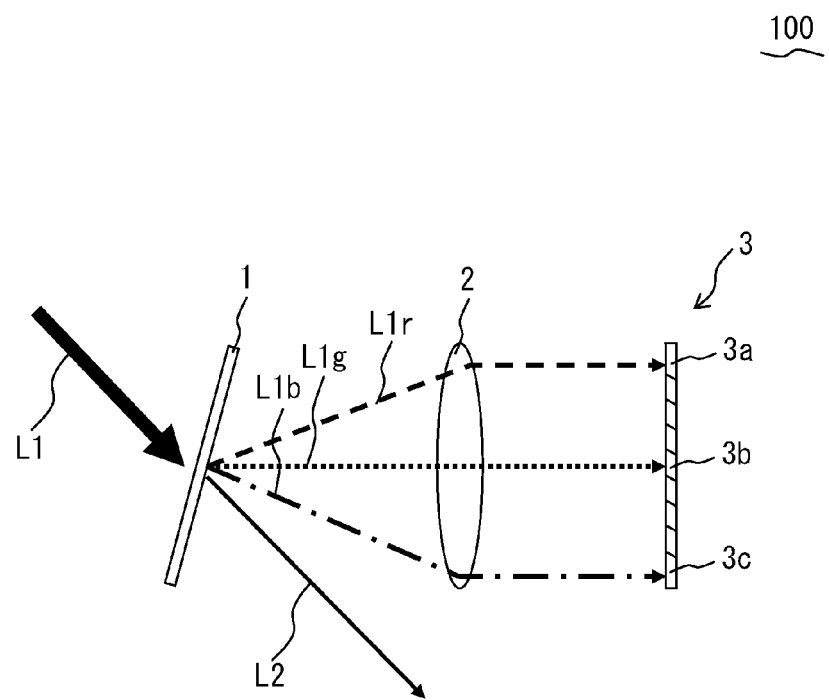
FIG. 1 exemplifies a configuration of a spectral device according to a prior art technology.

FIG. 1 exemplifies a configuration of a spectral device according to a prior art technology. Before explaining the spectral device according to the present embodiment, a spectral device 100 according to the prior art technology is briefly described with reference to FIG. 1.

A spectral device 100 related to the prior art technology exemplified in FIG. 1 includes: a transmissive diffraction grating 1 (diffraction element) which disperses received light for each wavelength; an optical condensing system 2 which condenses primary diffracted light generated by the diffraction in the diffraction grating 1; and a photo-detector 3 which includes a plurality of detection elements (detection element 3a, detection element 3b, and detection element 3c) arranged at the position where the primary diffracted light is condensed by the optical condensing system 2.

In the spectral device 100, the light L1 which has entered as a parallel luminous flux from an external unit is diffracted by the diffraction grating 1, and separated into zeroth-order diffracted light L2 which travels straight without diffraction and diffracted light of each order (excluding the zeroth order) which exits from the diffraction grating 1 at a different angle for each wavelength. Only the zeroth-order diffracted light L2, red primary-order diffracted light L1r, green primary-order diffracted light L1g, and blue primary-order diffracted light L1b are illustrated in FIG. 1.

The zeroth-order diffracted light and the diffracted light of each order exit as each parallel luminous flux from the diffraction grating 1 at a different angle of emergence. Therefore, the primary diffracted light which has entered the optical condensing system 2 is condensed for each wavelength at the photo-detector 3 arranged at the back focal position of the optical condensing system 2, and each of a plurality of detection elements of the photo-detector 3 detects the primary diffracted light of a different wavelength band. Thus, the spectral device 100 may acquire the wavelength information about the detected light. FIG. 1 illustrates the detection of the primary-order diffracted light L1r by the detection element 3a, the primary-order diffracted light L1g by the detection element 3b, and the primary-order diffracted light L1b by the detection element 3c.

Figure 2B:
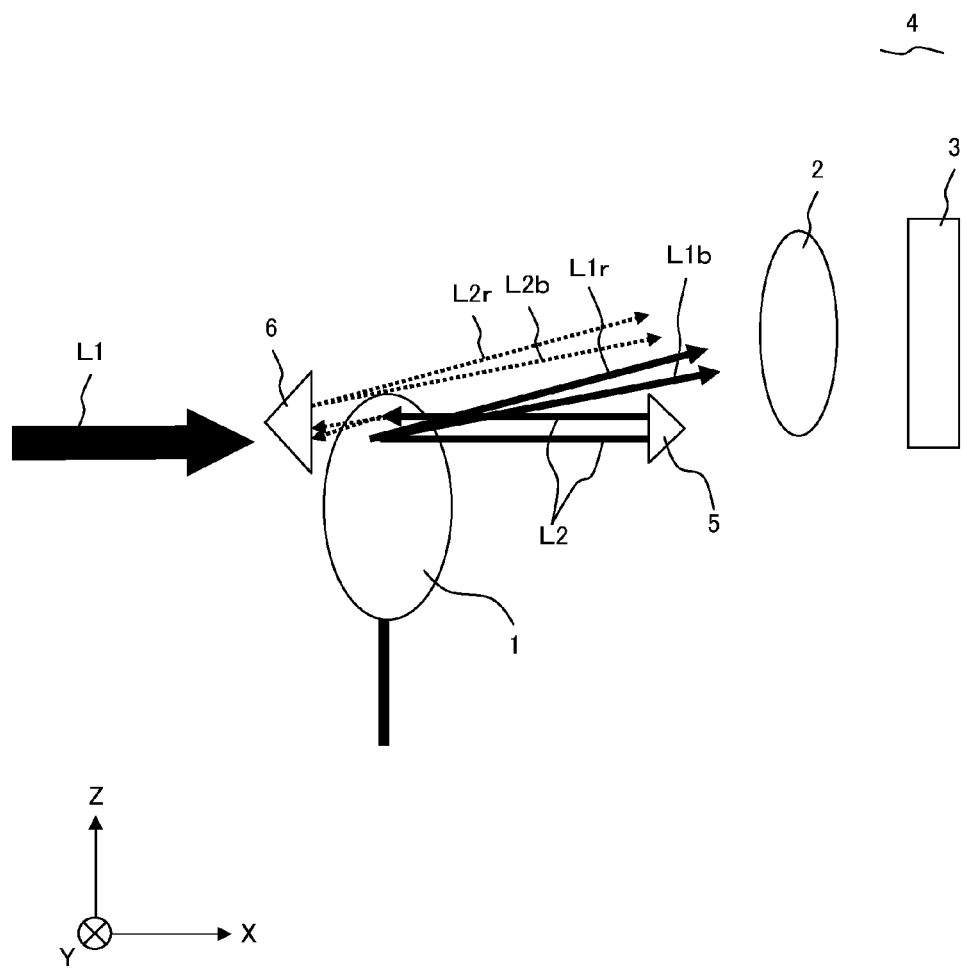
FIG. 2B is the outline of a side view of the spectral device according to the embodiment 1.

Next, a spectral device 4 according to the present embodiment is described below with reference to FIGS. 2A and 2B. FIG. 2A is the outline of a plan view of the spectral device according to the present embodiment. FIG. 2B is the outline of a side view of the spectral device according to the present embodiment. The X, Y, and Z coordinate systems in FIGS. 2A and 2B are orthogonal coordinate systems provided for convenience of reference of a direction.

The spectral device 4 exemplified in FIGS. 2A and 2B is different from the spectral device 100 exemplified in FIG. 1 in that two corner cubes (corner cubes 5 and 6) arranged opposite each other with the diffraction grating 1 interposed between them is included. The spectral device 4 is similar to the spectral device 100 in that it includes the diffraction grating 1, the optical condensing system 2, and the photo-detector 3 including a plurality of detection elements.

The corner cube 5 is a first deflection device which inverts the direction of travel of the zeroth-order diffracted light L2 (second light) generated by the diffraction of the light L1 (first light) which has entered the diffraction grating 1 as a parallel luminous flux from the outside of the spectral device 4, and leads the zeroth-order diffracted light L2 into the diffraction grating 1.

The corner cube 6 is a second deflection device which inverts the direction of travel of the primary diffracted light (primary-order diffracted light L2r, primary-order diffracted light L2b, etc.) generated by the diffraction of the zeroth-order diffracted light L2 which has entered the diffraction grating 1, thereby deflecting the primary diffracted light in the same direction as the primary diffracted light (primary-order diffracted light L1r, primary-order diffracted light L1b, etc.) generated by the diffraction of the light L1 and leading the deflected light into the optical condensing system 2.

In FIGS. 2A and 2B, for simplicity of attached drawings, only the red primary-order diffracted light L1r and the blue primary-order diffracted light L1b are illustrated as the primary diffracted light generated by the diffraction of the light L1, and only the red primary-order diffracted light L2r and the blue primary-order diffracted light L2b are illustrated as the primary diffracted light generated by the diffraction of the zeroth-order diffracted light L2. The primary diffracted light generated by the diffraction of the light L1 is hereafter referred to as a first primary-order diffracted light, and the primary diffracted light generated by the diffraction of the zeroth-order diffracted light L2 is hereafter referred to as a second primary-order diffracted light.

In the spectral device 4, the zeroth-order diffracted light L2 in which the direction of travel is inverted by the corner cube 5 enters the diffraction grating 1 from the surface opposite to the surface of the entrance of the light L1 (different surface from the light L1) at the same angle of incidence as the light L1. The second primary-order diffracted light generated by the diffraction of the zeroth-order diffracted light L2 travels in the opposite direction of the first primary-order diffracted light generated by the diffraction of the light L1 for each wavelength. However, by inverting the direction of travel by the corner cube 6, the second primary-order diffracted light travels the same direction as the first primary-order diffracted light for each wavelength, and enters the optical condensing system 2. Therefore, the first primary-order diffracted light and the second primary-order diffracted light are condensed at the same position by the optical condensing system 2 for each wavelength, and are detected by the photo-detector 3.

The corner cubes 5 and 6 invert the direction of travel of incident light as illustrated in FIGS. 2A and 2B, and slightly translate in parallel the incident light. Therefore, as illustrated in FIG. 2B, the second primary-order diffracted light enters the optical condensing system 2 without re-entrance into the diffraction grating 1 by the parallel translation of the zeroth-order diffracted light L2 by the corner cube 5 and the parallel translation of the second primary-order diffracted light by the corner cube 6.

Furthermore, the bar drawn downward the diffraction grating 1 in FIG. 2B indicates a rotation axis, and also indicates that the diffraction grating 1 may rotate on the rotation axis.

According to the spectral device 4 of the present embodiment, the corner cubes 5 and 6 enable the second primary-order diffracted light generated by the diffraction of the zeroth-order diffracted light L2 in addition to the first primary-order diffracted light generated by the diffraction of the light L1 to be detected by the photo-detector 3. Accordingly, high detection efficiency may be realized. Furthermore, since the spectral device 4 may re-diffract the zeroth-order diffracted light only by including the first and second deflection devices (corner cubes 5 and 6) which invert the direction of travel of light, high detection efficiency may be realized without excessively complicating the configuration of the spectral device.

Figure 3:
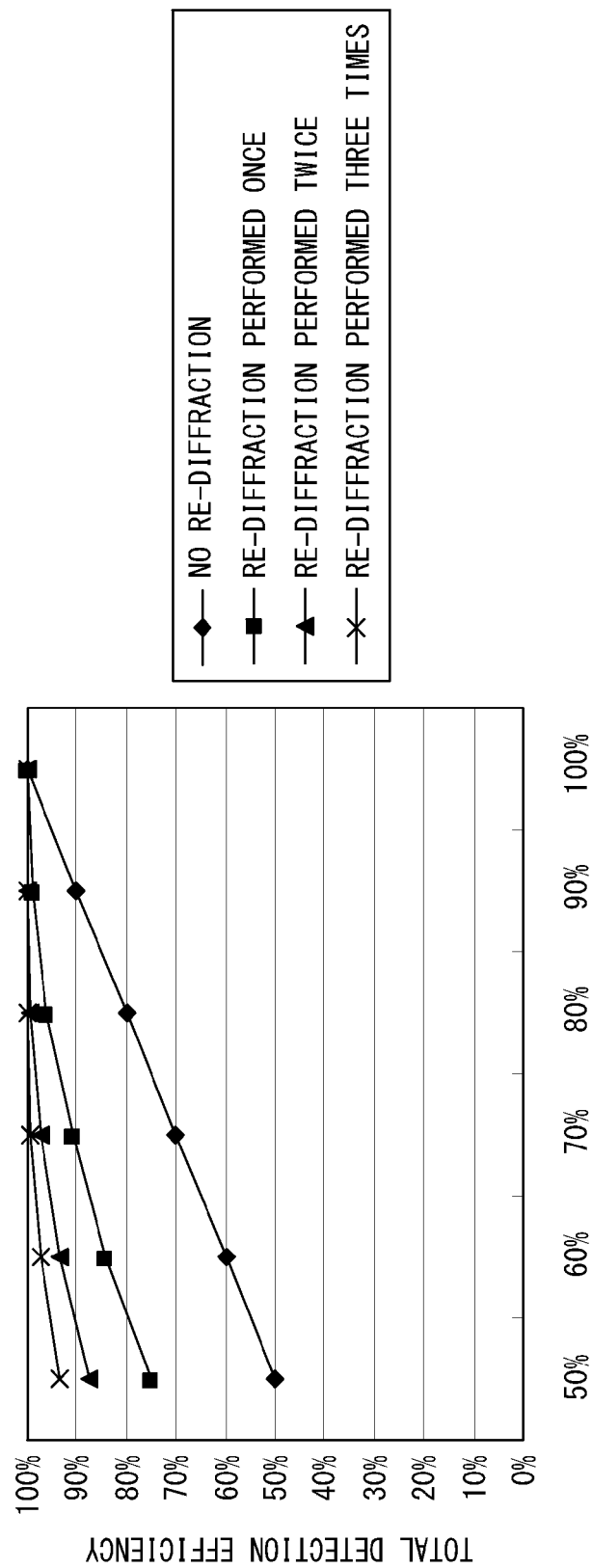
FIG. 3 illustrates the relationship between the frequency of re-diffraction and the diffraction efficiency.

Concretely, as illustrated in FIG. 3, for example, if the diffraction efficiency of the diffraction grating 1 is 50%, the total diffraction efficiency of the diffraction grating 1 is also 50% in the spectral device 100 of the configuration illustrated in FIG. 1 in which the zeroth-order diffracted light is not re-diffracted. Therefore, the detection efficiency of the spectral device 100 is about 50%. On the other hand, in the spectral device 4 according to the present embodiment, since the zeroth-order diffracted light is once re-diffracted, the total diffraction efficiency of the diffraction grating 1 is about 75%, and the detection efficiency of the spectral device 4 may be improved up to the same level. For example, if the diffraction grating 1 having the diffraction efficiency of about 70% is used, the detection efficiency of the spectral device 4 may be improved up to about 90%.

Furthermore, since the corner cubes are used in the present embodiment, strict angle adjustments are not required, thereby easily perform an assembly operation.

Figure 4B:
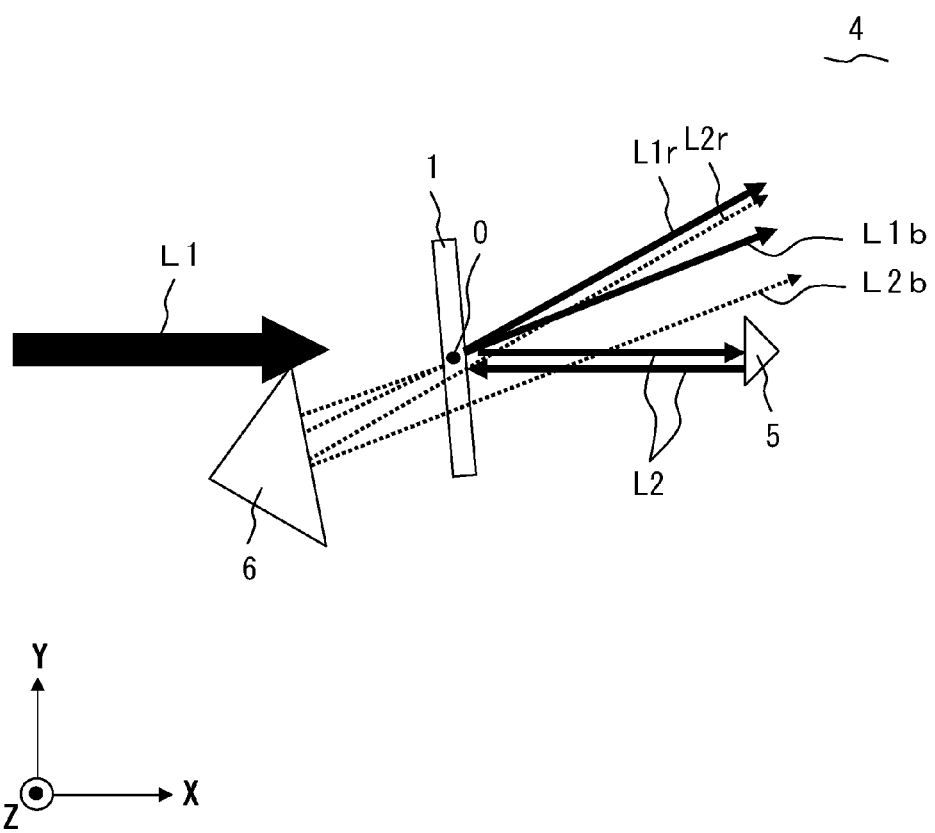
FIG. 4B is the outline of a plan view of the spectral device according to the embodiment 1 after the rotation of a diffraction element.

In addition, since the corner cubes 5 and 6 of the spectral device 4 function to invert the direction of travel of the incident light regardless of the angle of incidence, the angle of incidence of the light L1 and the angle of incidence of the zeroth-order diffracted light L2 constantly coincides with each other although the diffraction grating 1 is rotated, and the first primary-order diffracted light and the second primary-order diffracted light are condensed at the same position for each wavelength. Therefore, the diffraction grating 1 may be arranged as freely rotatable so that the angle of incidence of the light L1 may be changed. FIGS. 4A and 4B illustrate the states of the spectral device 4 before and after the rotation of the diffraction grating 1 arranged as freely rotatable on the rotation center O. The diffraction grating 1 is arranged so that the diffracted light of each order may be generated on the surface (XY surface) parallel to the sheet, has the rotation axis which is perpendicular to the sheet and matches the z-axis direction, and is configured as rotatable at an arbitrary angle using a stepping motor etc. By arranging the diffraction grating 1 as freely rotatable as illustrated in FIGS. 4A and 4B, the angle of incidence may be changed by rotating the diffraction grating 1. Therefore, the peak wavelength of the diffraction efficiency of the diffraction grating 1 may match the wavelength of the light to be detected. Accordingly, the light of a requested wavelength may be detected at high detection efficiency, and, for example, the angle of incidence may be adjusted depending on a fluorescent substance etc. when applied to a fluorescent microscope.

In the present embodiment, the higher the diffraction efficiency of a diffraction element is, the higher the detection efficiency of a spectral device becomes. Therefore, a diffraction element having higher diffraction efficiency is preferable. For example, a transmissive volume phase holographic grating is more preferable.

Although the spectral device 4 which detects the primary diffracted light and in which the optical condensing system 2 is arranged at the position of the entrance of the primary diffracted light is exemplified in the present embodiment, the spectral device may detect diffracted light of any order instead of the primary diffracted light.

Embodiment 2

Figure 5A:
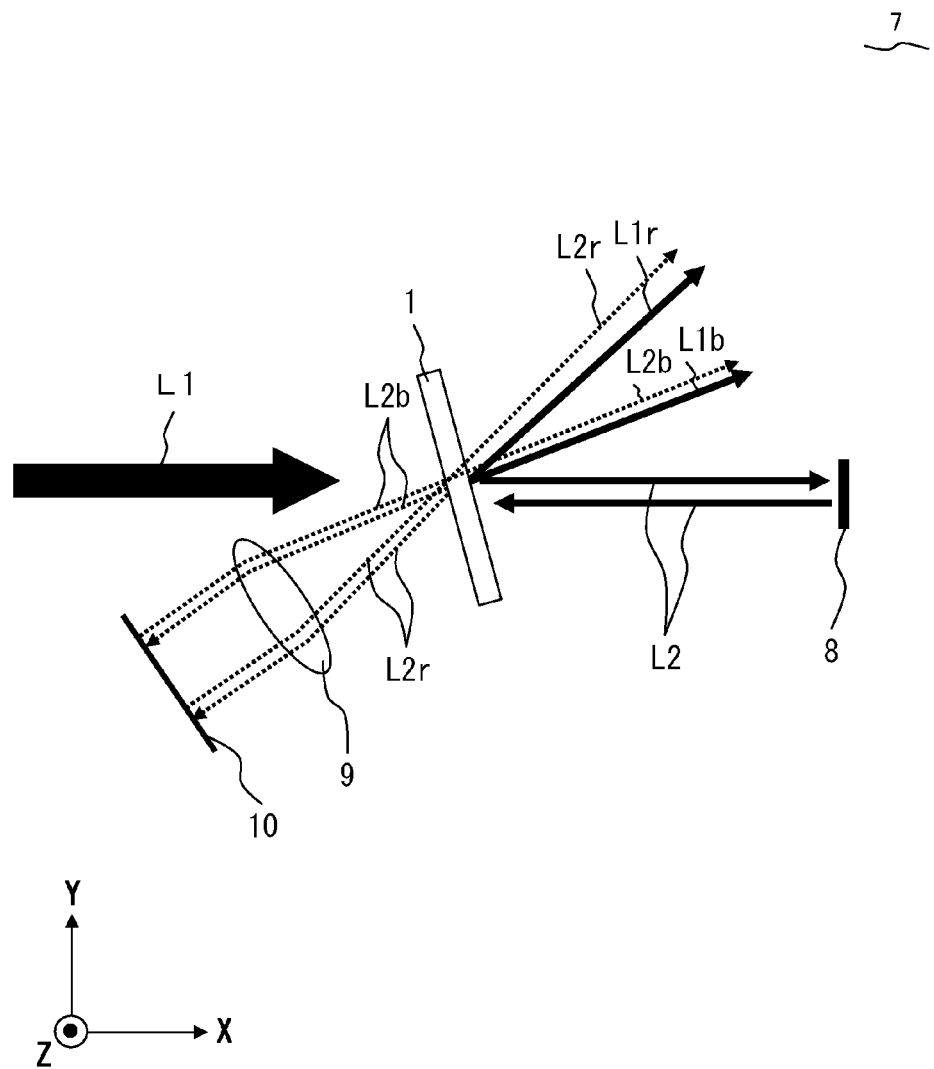
FIG. 5A is the outline of a plan view of the spectral device according to the embodiment 2.
Figure 5B:
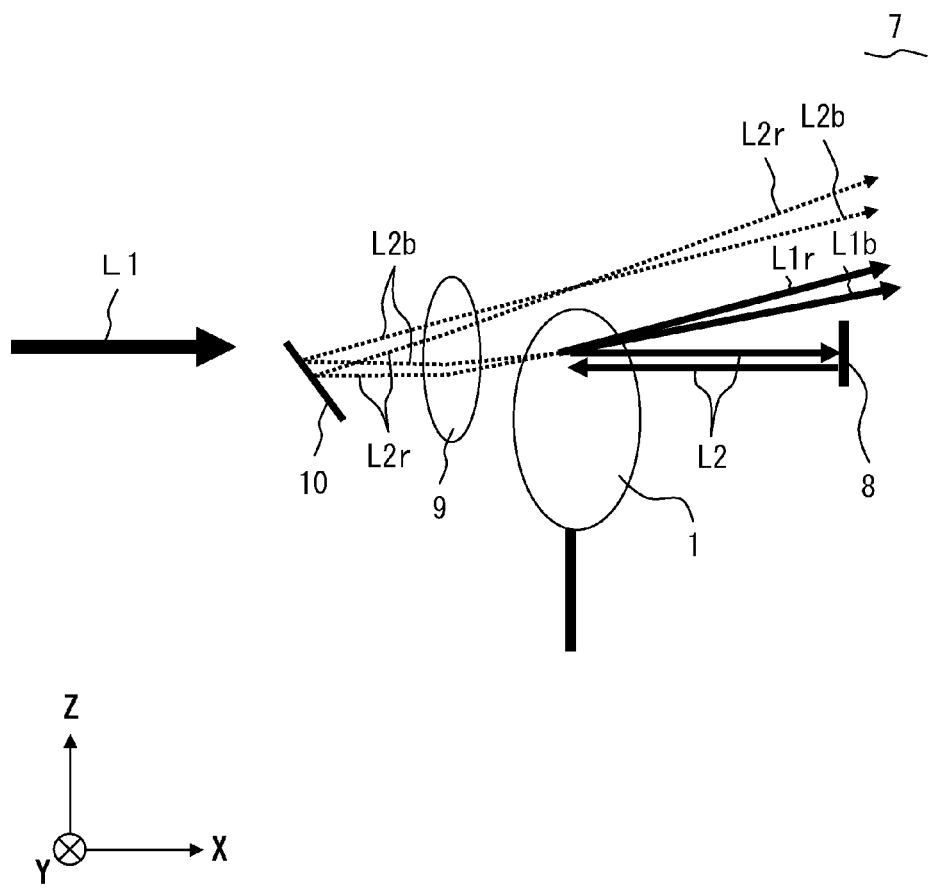
FIG. 5B is the outline of a side view of the spectral device according to the embodiment 2.

FIG. 5A is the outline of a plan view of the spectral device according to the present embodiment. FIG. 5B is the outline of a side view of the spectral device according to the present embodiment. The X, Y, and Z coordinate systems in FIGS. 5A and 5B are orthogonal coordinate systems provided for convenience of reference of a direction. In FIGS. 5A and 5B, the optical condensing system 2 and the photo-detector 3 are omitted.

A spectral device 7 exemplified in FIGS. 5A and 5B is different from the spectral device 4 according to the embodiment 1 in that the corner cube 5 is replaced with a mirror 8, and the corner cube 6 is replaced with an optical condensing system configured by a lens etc. and a mirror 10. Other configurations are the same as the spectral device 4 according to the embodiment 1. The spectral device 7 according to the present embodiment is described below with reference to FIGS. 5A and 5B.

The mirror 8 is arranged to allow the zeroth-order diffracted light L2 generated by the diffraction of the light L1 which has entered the diffraction grating 1 to perpendicularly enter the mirror 8. Therefore, the mirror 8 functions as the first deflection device which allows the zeroth-order diffracted light L2 to enter the diffraction grating 1 by inverting the direction of travel of the zeroth-order diffracted light L2. The mirror 8 may be replaced with a triangular prism.

The optical condensing system 9 is an optical condensing system having a front focal position at the position where the light L1 enters the diffraction grating 1. The mirror 10 is a reflective member arranged at a back focal position of the optical condensing system 9. With the arrangement above made with the set positions, the optical condensing system 9 and the mirror 10 function to invert the direction of travel of the second primary-order diffracted light regardless of the angle of incidence to the optical condensing system 9. That is, the optical condensing system 9 and the mirror 10 function as a second deflection device which deflects the second primary-order diffracted light in the same direction as the first primary-order diffracted light and leads the light into the optical condensing system 2 not illustrated in the attached drawings. The spectral device 7 according to the present embodiment includes two optical condensing systems. The optical condensing system 2 not illustrated in the attached drawings is a first optical condensing system, and the optical condensing system 9 is a second optical condensing system.

Since the second deflection device is configured by an optical condensing system and a mirror in the present embodiment, the spectral device 7 may be produced at a low cost.

With the spectral device 7 configured as described above, the first primary-order diffracted light and the second primary-order diffracted light travel in the same direction for each wavelength. Therefore, as with the spectral device 4 according to the embodiment 1, the photo-detector 3 may detect the second primary-order diffracted light in addition to the first primary-order diffracted light, thereby realizing high detection efficiency. The spectral device 7 according to the present embodiment is also similar to the spectral device 4 according to the embodiment 1 in that the configuration of the spectral device may be free of excessively complicated configuration.

The spectral device 7 may also condense the first primary-order diffracted light and the second primary-order diffracted light at the same position for each wavelength regardless of the angle of incidence to the diffraction grating 1. Therefore, the spectral device 7 according to the present embodiment is also similar to the spectral device 4 according to the embodiment 1 in that the peak wavelength of the diffraction efficiency of the diffraction grating 1 may coincide with the wavelength of the light to be detected by arranging the diffraction grating 1 as freely rotatable to change the angle of incidence of the light L1. Therefore, the light of a requested wavelength may be detected at high detection efficiency.

Embodiment 3

Figure 6A:
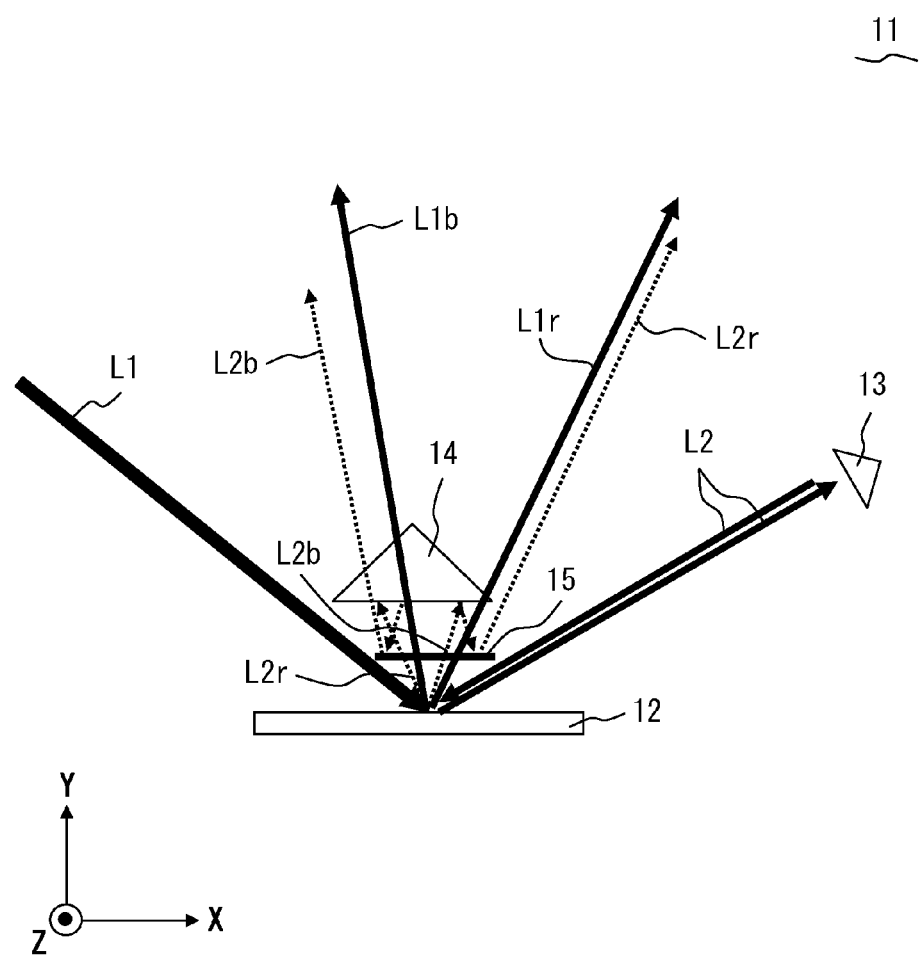
FIG. 6A is the outline of a plan view of the spectral device according to the embodiment 3.
Figure 6B:
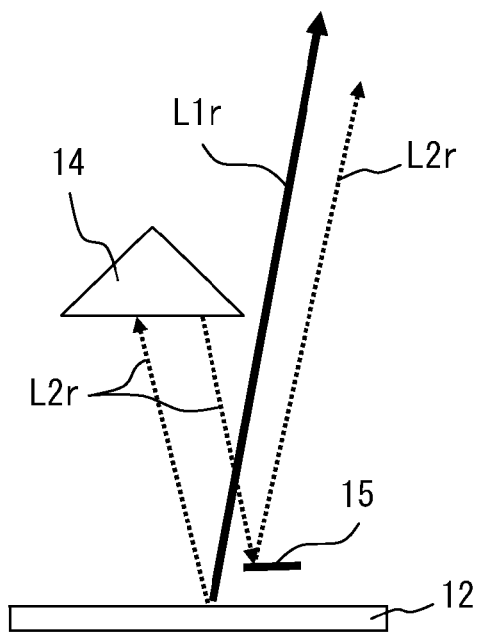
FIG. 6B is the outline of a side view of the spectral device according to the embodiment 3.

FIG. 6A is the outline of a plan view of the spectral device according to the present embodiment. FIG. 6B is the outline of a side view of the spectral device according to the present embodiment. The X, Y, and Z coordinate systems in FIGS. 6A and 6B are orthogonal coordinate systems provided for convenience of reference of a direction. In FIGS. 6A and 6B, the optical condensing system 2 and the photo-detector 3 are omitted.

A spectral device 11 exemplified in FIGS. 6A and 6B is different from the spectral device 4 according to the embodiment 1 in that the transmissive diffraction grating 1 is replaced with the a reflective diffraction grating 12, the corner cube 5 is replaced with a corner cube 13, and the corner cube 6 is replaced with a corner cube 14 and a mirror 15. The spectral device 11 according to the present embodiment is described below with reference to FIGS. 6A and 6B.

The corner cube 13 is a first deflection device which inverts the direction of travel of the zeroth-order diffracted light L2 generated by the diffraction of the light L1 which has entered the diffraction grating 12 as a parallel luminous flux from the outside of the spectral device 11, and leads the zeroth-order diffracted light L2 into the diffraction grating 12. Since the zeroth-order diffracted light L2 is generated in the direction of the regular reflection of the light L1, the zeroth-order diffracted light L2 whose direction of travel has been inverted by the corner cube 13 enters the diffraction grating 12 at the same angle of incidence as the light L1. That is, the corner cube 13 is different from the corner cube 5 of the spectral device 4 in that the zeroth-order diffracted light L2 is led into the diffraction grating 12 from the same surface as the light L1.

The corner cube 14 is an inversion member which inverts the direction of travel of the second primary-order diffracted light generated by the diffraction of the zeroth-order diffracted light L2. The mirror 15 is a reflective member which reflects the second primary-order diffracted light whose direction of travel has been inverted by the corner cube 14, and arranged near the diffraction grating 12. Assuming that the light L1 and the zeroth-order diffracted light L2 enters at the same angle of incidence symmetrically about the normal of the diffraction grating 12, and that the first primary-order diffracted light and the second primary-order diffracted light exit symmetrically about the normal of the diffraction grating 12, the corner cube 14 and the mirror 15 function as the second deflection device which deflects the second primary-order diffracted light in the same direction as the first primary-order diffracted light on the whole, and leads the deflected light into the optical condensing system 2 not illustrated in the attached drawings.

The configuration of arranging the mirror 15 near the diffraction grating 12 is preferable in that the second primary-order diffracted light which has been reflected by the mirror 15 may be prevented from entering the corner cube 14 again. That is, "near the diffraction grating 12" refers to the position close to the diffraction grating 12 where the second primary-order diffracted light which has been reflected by the mirror 15 does not enter the corner cube 14 again.

In the spectral device 11, the zeroth-order diffracted light L2 whose direction of travel has been inverted by the corner cube 13 enters the diffraction grating 12 at the same angle of incidence as the light L1 from the same surface of incidence as the light L1. The second primary-order diffracted light generated by the diffraction of the zeroth-order diffracted light L2 travels in the symmetrical direction about the normal of the diffraction grating 12 with respect to the first primary-order diffracted light generated by the diffraction of the light L1 for each wavelength. Afterwards, the direction of travel of the second primary-order diffracted light is inverted by the corner cube 6, and the light is then regularly reflected by the mirror 15, thereby traveling in the same direction as the first primary-order diffracted light for each wavelength, and entering the optical condensing system 2. Therefore, the first primary-order diffracted light and the second primary-order diffracted light are condensed by the optical condensing system 2 at the same position for each wavelength, and detected by the photo-detector 3.

With the spectral device 11 as configured above, the first primary-order diffracted light and the second primary-order diffracted light travel in the same direction for each wavelength. Therefore, as with the spectral device 4 according to the embodiment 1, in addition to the first primary-order diffracted light, the second primary-order diffracted light may be detected by the photo-detector 3, thereby realizing high detection efficiency. The device is also similar to the spectral device 4 according to the embodiment 1 in that the spectral device is free of an excessively complicated configuration.

Figure 7B:
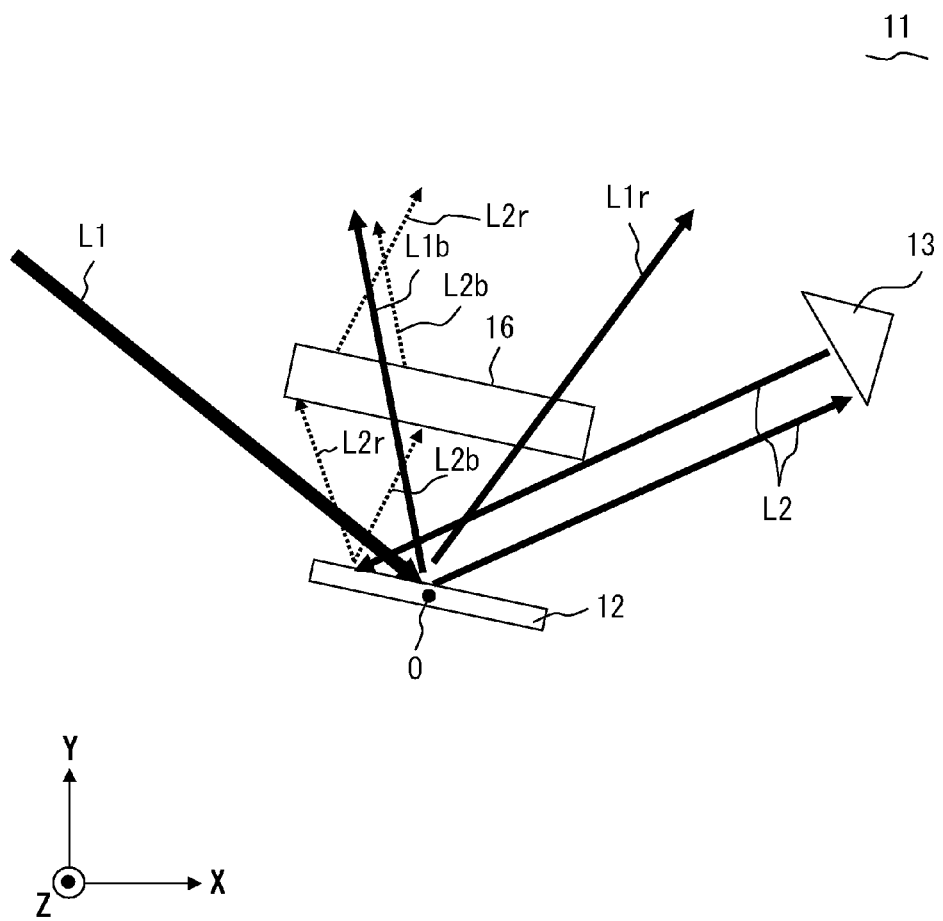
FIG. 7B is the outline of a plan view of the spectral device according to the embodiment 3 after rotating the diffraction element.

Furthermore, the spectral device 11 also functions to allow the corner cube 13 to invert the direction of travel of the incident light regardless of the angle of incidence, and functions to allow a deflection device 16 configured by the corner cube 14 and the mirror 15 to invert the direction of travel of the incident light totally regardless of the angle of incidence. Therefore, the angle of incidence of the light L1 and the angle of incidence of the zeroth-order diffracted light L2 constantly coincide with each other although the diffraction grating 12 is rotated, and the first primary-order diffracted light and the second primary-order diffracted light condenses at the same position for each wavelength. Therefore, the diffraction grating 12 may be arranged as freely rotatable so that the angle of incidence of the light L1 may be changed. FIGS. 7A and 7B illustrate the state of the spectral device 11 before and after the rotation of the diffraction grating 12 arranged as freely rotatable on the rotation center O, and the corner cube 14 and the mirror 15 are illustrated as the deflection device 16. By arranging the diffraction grating 12 as illustrated in FIGS. 7A and 7B, the diffraction grating 12 may be rotated to change the angle of incidence, thereby coinciding the peak wavelength of the diffraction efficiency of the diffraction grating 12 with the wavelength of the light to be detected. Therefore, the light of a requested wavelength may be detected at high detection efficiency.

Thus, the spectral device 11 provided with the diffraction grating 12 may obtain the effect of the spectral device 4 provided with the transmissive diffraction grating 1 only by practically adding the reflective member (mirror 15) for regularly reflecting the second primary-order diffracted light.

Embodiment 4

Figure 8B:
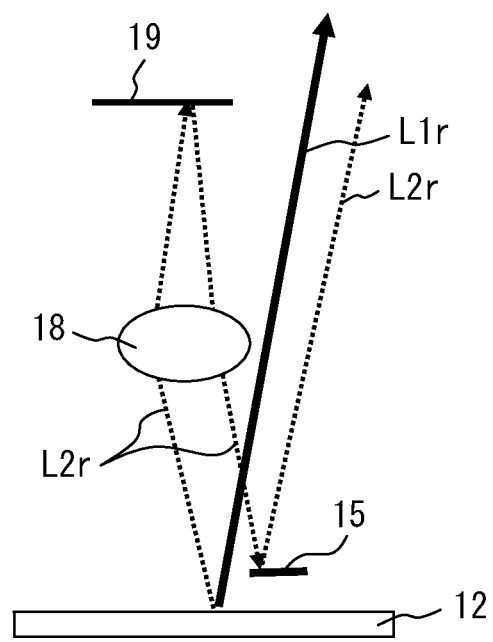
FIG. 8B is the outline of a side view of the spectral device according to the embodiment 4.

FIG. 8A is the outline of a plan view of the spectral device according to the present embodiment. FIG. 8B is the outline of a side view of the spectral device according to the present embodiment. The X, Y, and Z coordinate systems in FIGS. 8A and 8B are orthogonal coordinate systems provided for convenience of reference of a direction. In FIGS. 8A and 8B, the optical condensing system 2 and the photo-detector 3 are omitted.

A spectral device 17 exemplified in FIGS. 8A and 8B is different from the spectral device 11 according to the embodiment 3 in that the corner cube 14 is replaced with an optical condensing system 18 and a mirror 19. Other configurations are similar to those of the spectral device 11 according to the embodiment 3. The spectral device 17 according to the present embodiment is described below with reference to FIGS. 8A and 8B.

The optical condensing system 18 has a front focal position at the position where the light L1 enters the diffraction grating 1. In addition, the mirror 19 is a reflective member arranged at a back focal position of the optical condensing system 18. With the arrangement of the positions, the optical condensing system 18 and the mirror 19 function so that the direction of travel of the second primary-order diffracted light may be inverted regardless of the angle of incidence to the optical condensing system 18. That is, the mirror 15 as a reflective member arranged near the diffraction grating 12 which reflects the second primary-order diffracted light and the optical condensing system 18 and the mirror 19 which invert the direction of travel of the second primary-order diffracted light totally function as the second deflection device which deflects the second primary-order diffracted light in the same direction as the first primary-order diffracted light, and allows the deflected light to enter the optical condensing system 2 not illustrated in the attached drawings. The spectral device 17 according to the present embodiment includes two optical condensing systems. The optical condensing system 2 not illustrated in the attached drawings is the first optical condensing system and the optical condensing system 18 is the second optical condensing system.

With the spectral device 17 configured as described above, the first primary-order diffracted light and the second primary-order diffracted light travel in the same direction for each wavelength. Therefore, as with the spectral device 11 according to the embodiment 3, the photo-detector 3 may detect the second primary-order diffracted light in addition to the first primary-order diffracted light, thereby realizing high detection efficiency. The spectral device 17 is also similar to the spectral device 11 according to the embodiment 3 in that the configuration of the spectral device is not excessively complicated.

Furthermore, the spectral device 17 may condense the first primary-order diffracted light and the second primary-order diffracted light at the same position for each wavelength regardless of the angle of incidence to the diffraction grating 12. Therefore, by arranging the diffraction grating 12 as freely rotating so that the angle of incidence of the light L1 may be changed, the peak wavelength of the diffraction efficiency of the diffraction grating 12 may coincide with the wavelength of the light to be detected, which is similar to the spectral device 11 according to the embodiment 3. Therefore, the light of requested wavelength may be detected at high detection efficiency.

Embodiment 5

Figure 9:
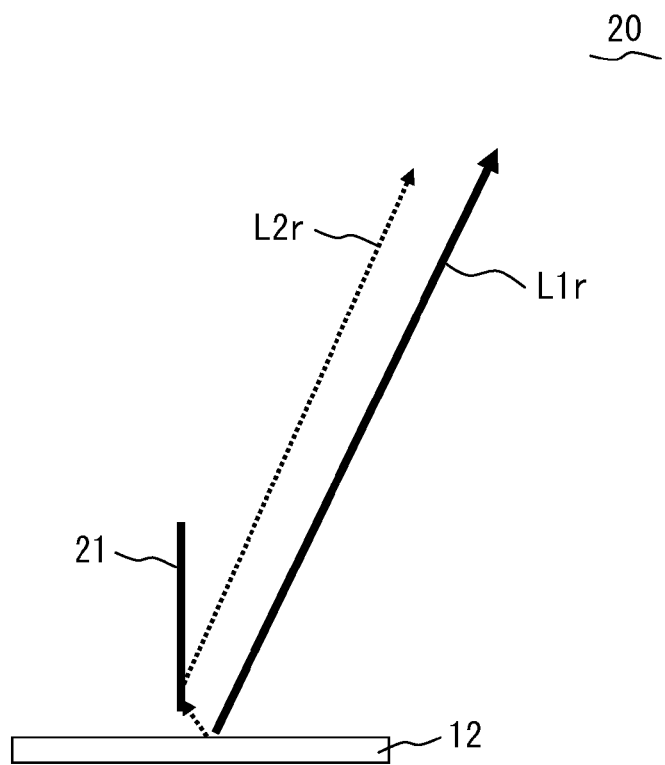
FIG. 9 is the outline of a side view of the spectral device according to the embodiment 5.

FIG. 9 is the outline of a side view of the spectral device according to the present embodiment. The XYZ coordinate system in FIG. 9 is an orthogonal coordinate system provided for convenience of reference of a direction. In FIG. 9, the optical condensing system 2 and the photo-detector 3 are omitted.

A spectral device 20 exemplified in FIG. 9 is different from the spectral device 11 according to the embodiment 3 in that the corner cube 14 and the mirror 15 are replaced with a mirror 21. Other configurations are similar to the spectral device 11 according to the embodiment 3. The spectral device 20 according to the present embodiment is described below with reference to FIG. 9.

The mirror 21 functions as a second deflection device which deflects the second primary-order diffracted light in the same direction as the first primary-order diffracted light by making an arrangement with an adjusted angle, and allows the second primary-order diffracted light to enter the optical condensing system 2 not illustrated in the attached drawings. However, the light having a wavelength of the same direction of diffraction as the light L1 with respect to the incident position is not re-diffracted.

With the spectral device 20 as configured above, the first primary-order diffracted light and the second primary-order diffracted light travel in the same direction for each wavelength. Therefore, as with the spectral device 11 according to the embodiment 3, in addition to the first primary-order diffracted light, the second primary-order diffracted light may be detected by the photo-detector 3, thereby realizing high detection efficiency. The device is also similar to the spectral device 11 according to the embodiment 3 in that the spectral device is free of an excessively complicated configuration.

Embodiment 6

Figure 10:
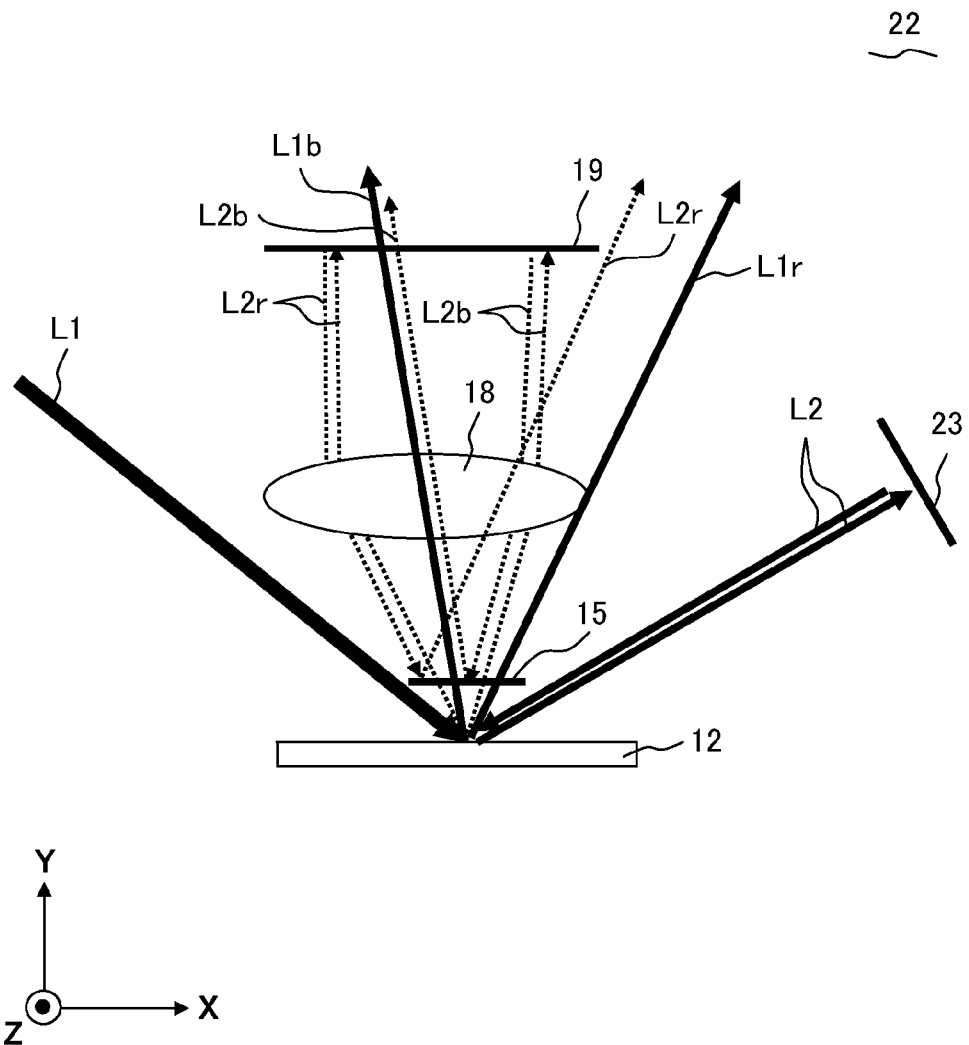
FIG. 10 is the outline of a plan view of the spectral device according to the embodiment 6.

FIG. 10 is the outline of a plan view of the spectral device according to the present embodiment. The XYZ coordinate system in FIG. 10 is an orthogonal coordinate system provided for convenience of reference of a direction. In FIG. 10, the optical condensing system 2 and the photo-detector 3 are omitted.

A spectral device 22 exemplified in FIG. 10 is different from the spectral device 17 according to the embodiment 4 in that the corner cube 13 is replaced with a mirror 23. Other configurations are similar to the spectral device 17 according to the embodiment 4. The mirror 23 may be replaced with a triangular prism.

Figure 11A:
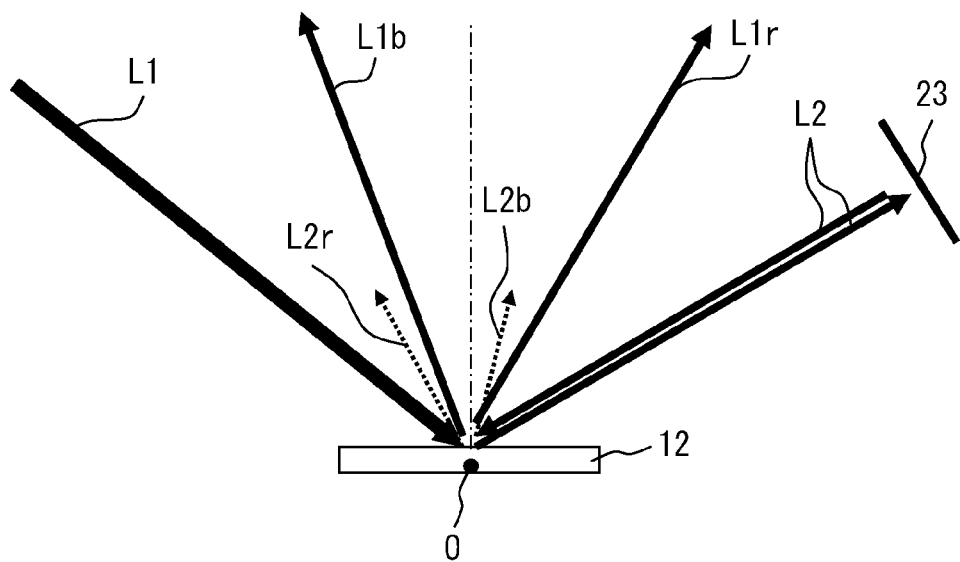
FIG. 11A is the outline of a plan view of the spectral device according to the embodiment 6 before rotating the diffraction element.
Figure 11A:
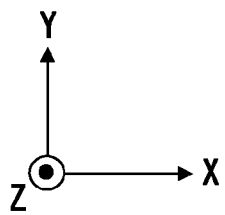
Figure 11B:
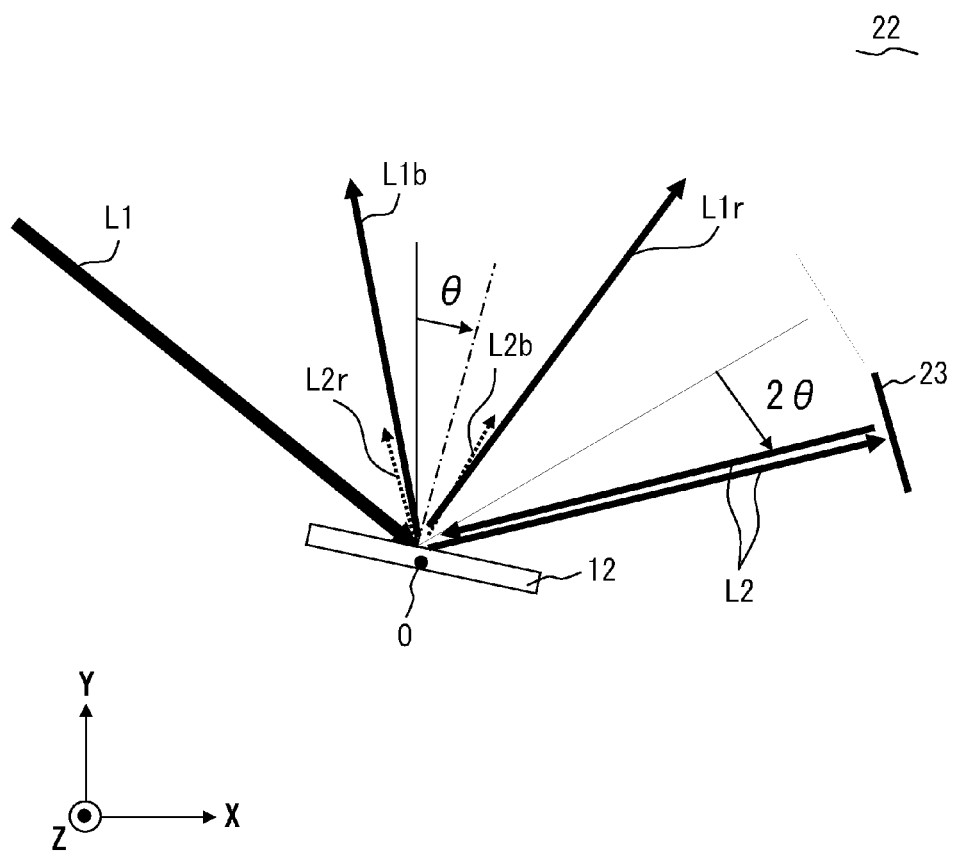
FIG. 11B is the outline of a plan view of the spectral device according to the embodiment 6 after rotating the diffraction element.

The diffraction grating 12 is arranged rotatably about the rotation center O, and FIGS. 11A and 11B illustrate the state of the spectral device 22 before and after the rotation of the diffraction grating 12.

The mirror 23 is a reflective member which travels with the rotation of the diffraction grating 12 as illustrated in FIG. 11B while rotating at an angle of 2θ which is twice the rotation angle of θ of the diffraction grating 12 on the rotation axis (rotation center O) of the diffraction grating 12. The zeroth-order diffracted light L2 perpendicularly enters the mirror 23 regardless of the rotation angle of the diffraction grating 12 by the mirror 23 operating with the rotation of the diffraction grating 12 as described above. Therefore, the mirror 23 functions as the first deflection device which inverts the direction of travel of the zeroth-order diffracted light L2 and allows the zeroth-order diffracted light L2 to enter the diffraction grating 12.

The unitary construction of the mirror 19 and the optical condensing system 18 according to the present embodiment and the deflection device 16 according to the embodiment 3 are configured as rotating coaxially with the rotation axis of the diffraction grating 12 by the same angle of θ as the rotation angle of θ of the diffraction grating 12.

Also by the spectral device 22 configured as described above, the first primary-order diffracted light and the second primary-order diffracted light travels in the same direction for each wavelength. Therefore, as with the spectral device 17 according to the embodiment 4, the second primary-order diffracted light in addition to the first primary-order diffracted light may be detected by the photo-detector 3. Accordingly, high detection efficiency may be realized. The spectral device 22 is similar to the spectral device 17 according to the embodiment 4 also in that the configuration of the spectral device may be prevented from being excessively complicated.

Furthermore, the spectral device 22 may condense the first primary-order diffracted light and the second primary-order diffracted light at the same position for each wavelength regardless of the angle of incidence to the diffraction grating 12. Therefore, the spectral device 22 is similar to the spectral device 17 according to the embodiment 4 in that the peak wavelength of the diffraction efficiency of the diffraction grating 12 may coincide with the wavelength of the light to be detected by arranging the diffraction grating 12 as freely rotatable so that the angle of incidence of the light L1 may be changed. Therefore, the light of a requested wavelength may be detected with high detection efficiency.

Embodiment 7

Figure 12A:
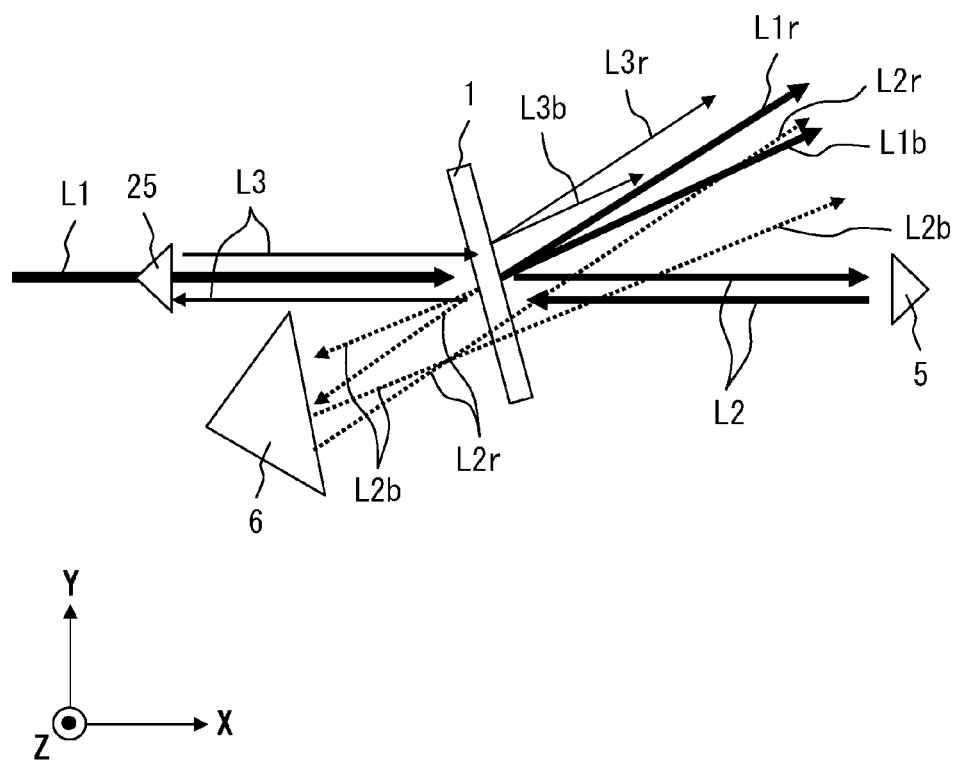
FIG. 12A is the outline of a plan view of the spectral device according to the embodiment 7.
Figure 12B:
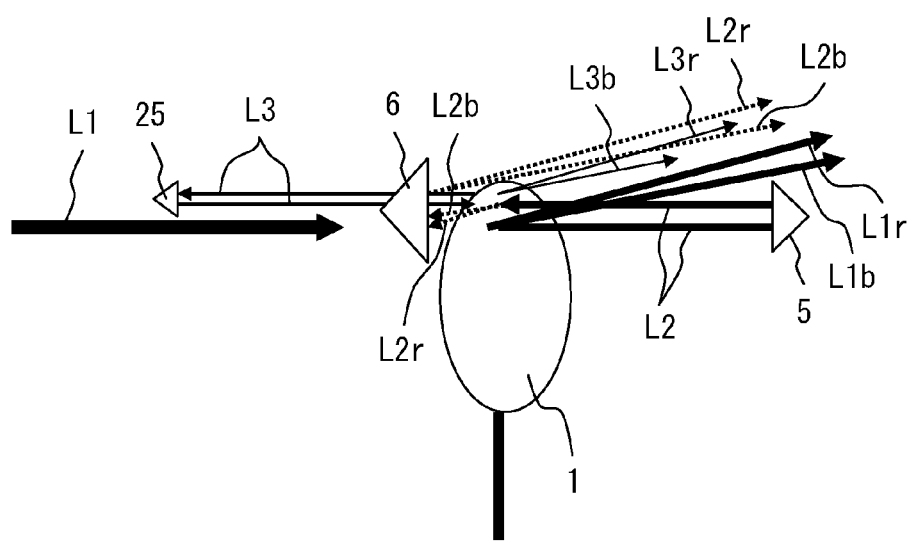
FIG. 12B is the outline of a side view of the spectral device according to the embodiment 7.

FIG. 12A is the outline of a plan view of the spectral device according to the present embodiment. FIG. 12B is the outline of a side view of the spectral device according to the present embodiment. The X, Y, and Z coordinate systems in FIGS. 12A and 12B are orthogonal coordinate systems provided for convenience of reference of a direction. In FIGS. 12A and 12B, the optical condensing system 2 and the photo-detector 3 are omitted.

A spectral device 24 exemplified in FIGS. 12A and 12B is different from the spectral device 4 according to the embodiment 1 in that a corner cube 25 is included. Other configurations are the same as the spectral device 4 according to the embodiment 1. The spectral device 24 according to the present embodiment is described below with reference to FIGS. 12A and 12B.

The corner cube 25 is a third deflection device which inverts the direction of travel of zeroth-order diffracted light L3 generated by the diffraction of the zeroth-order diffracted light L2 to allow the zeroth-order diffracted light L3 to enter the diffraction grating 1. The corner cube 25 is arranged not to interrupt the light L1. The arrangement may be realized by parallel translation of the zeroth-order diffracted light L2 by the corner cube 5.

In a spectral device 24, the zeroth-order diffracted light L3 whose direction of travel has been inverted by the corner cube 25 enters the diffraction grating 1 at the same angle of incidence as the light L1 from the same incident surface as the light L1. Third primary-order diffracted light (primary-order diffracted light L3r, primary-order diffracted light L3b) generated by the diffraction of the zeroth-order diffracted light L3 travels in the same distance as the first primary-order diffracted light generated by the diffraction of the light L1 for each wavelength, and enters the optical condensing system 2. Therefore, the first primary-order diffracted light, the second primary-order diffracted light, and the third primary-order diffracted light are condensed by the optical condensing system 2 at the same position for each wavelength, and detected by the photo-detector 3.

According to the spectral device 24 of the present embodiment, the photo-detector 3 may detect the third primary-order diffracted light generated by the diffraction of the zeroth-order diffracted light L3 in addition to the first primary-order diffracted light generated by the diffraction of the light L1 and the second primary-order diffracted light generated by the diffraction of the zeroth-order diffracted light L2. Therefore, the spectral device 24 may realize higher detection efficiency than the spectral device 4 according to the embodiment 1. Furthermore, the difference in configuration between the spectral device 24 and the spectral device 4 is only that the spectral device 24 includes the corner cube 25. Therefore, the configuration of the spectral device may be free of an excessive complicated configuration, and realize higher detection efficiency.

Concretely, as illustrated in FIG. 3, if the diffraction efficiency of the diffraction grating 1 is 50%, the total diffraction efficiency of the diffraction grating 1 is about 75% in the spectral device 4 according to the embodiment 1 in which the zeroth-order diffracted light is once re-diffracted, thereby acquiring almost equal detection efficiency of the spectral device 4. On the other hand, the total diffraction efficiency of the diffraction grating 1 is lower than 90% in the spectral device 24 according to the present embodiment in which the zeroth-order diffracted light is re-diffracted twice, thereby improving the detection efficiency of the spectral device 24 up to the same level.

Furthermore, since the zeroth-order diffracted light L3 enters the diffraction grating 1 at the same angle as the light L1 regardless of the rotation angle of the diffraction grating 1, the first primary-order diffracted light, the second primary-order diffracted light, and the third primary-order diffracted light may be condensed at the same position for each wavelength. Therefore, the spectral device 24 is similar to the spectral device 4 according to the embodiment 1 in that the peak wavelength of the diffraction efficiency of the diffraction grating 1 may coincide with the wavelength of the light to be detected by arranging the diffraction grating 1 as freely rotatable so that the angle of incidence of the light L1 may be changed. Therefore, the light of a requested wavelength may be detected with high detection efficiency.

The corner cube 5 may be replaced with a triangular prism, and the corner cube 25 may be replaced with a mirror or a triangular prism.

Embodiment 8

Figure 13:
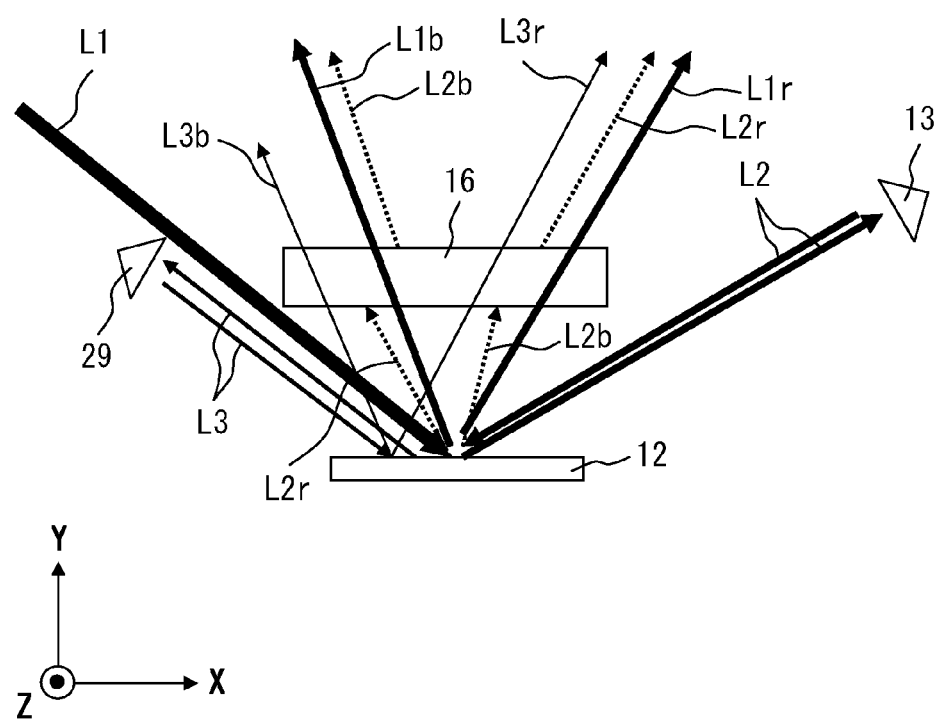
FIG. 13 is the outline of a plan view of the spectral device according to the embodiment 8.

FIG. 13 is the outline of a plan view of the spectral device according to the present embodiment. The X, Y, and Z coordinate systems in FIG. 13 is an orthogonal coordinate system provided for convenience of reference of a direction. In FIG. 13, the optical condensing system 2 and the photo-detector 3 are omitted.

A spectral device 28 exemplified in FIG. 13 is different from the spectral device 11 according to the embodiment 3 in that a corner cube 29 is included. Other configurations are the same as the spectral device 11 according to the embodiment 3. The spectral device 28 according to the present embodiment is described below with reference to FIG. 13.

The corner cube 29 is a third deflection device which inverts the direction of travel of zeroth-order diffracted light L3 generated by the diffraction of the zeroth-order diffracted light L2 to allow the zeroth-order diffracted light L3 to enter the diffraction grating 12.

In a spectral device 28, the zeroth-order diffracted light L3 whose direction of travel has been inverted by the corner cube 29 enters the diffraction grating 12 at the same angle of incidence as the light L1 from the same incident surface as the light L1. Third primary-order diffracted light (primary-order diffracted light L3r, primary-order diffracted light L3b) generated by the diffraction of the zeroth-order diffracted light L3 travels in the same direction as the first primary-order diffracted light generated by the diffraction of the light L1 for each wavelength, and enters the optical condensing system 2. Therefore, the first primary-order diffracted light, the second primary-order diffracted light, and the third primary-order diffracted light are condensed by the optical condensing system 2 at the same position for each wavelength, and detected by the photo-detector 3.

According to the spectral device 28 of the present embodiment, the photo-detector 3 may detect the third primary-order diffracted light generated by the diffraction of the zeroth-order diffracted light L3 in addition to the first primary-order diffracted light generated by the diffraction of the light L1 and the second primary-order diffracted light generated by the diffraction of the zeroth-order diffracted light L2. Therefore, the spectral device 28 may realize higher detection efficiency than the spectral device 11 according to the embodiment 3. Furthermore, the difference in configuration between the spectral device 28 and the spectral device 11 is only that the spectral device 28 includes the corner cube 29. Therefore, the configuration of the spectral device may be free of an excessive complicated configuration, and realize higher detection efficiency.

Furthermore, since the zeroth-order diffracted light L3 enters the diffraction grating 12 at the same angle as the light L1 regardless of the rotation angle of the diffraction grating 12, the first primary-order diffracted light, the second primary-order diffracted light, and the third primary-order diffracted light may be condensed at the same position for each wavelength. Therefore, the spectral device 28 is similar to the spectral device 11 according to the embodiment 3 in that the peak wavelength of the diffraction efficiency of the diffraction grating 12 may coincide with the wavelength of the light to be detected by arranging the diffraction grating 12 as freely rotatable so that the angle of incidence of the light L1 may be changed. Therefore, the light of a requested wavelength may be detected with high detection efficiency.

The corner cube 5 may be replaced with a triangular prism, and the corner cube 29 may be replaced with a mirror or a triangular prism.

The embodiments above exemplify the configuration in which the zeroth-order diffracted light is once or twice re-diffracted, but the spectral device may be re-diffracted three or more times. However, it is preferable to select the frequency of the re-diffraction by considering that satisfactory detection efficiency may be acquired by the re-diffraction of two times or so when the diffraction efficiency of a detection element is somewhat high, and that the higher the frequency of the re-diffraction is, the more complicated the configuration becomes.

Embodiment 9

Figure 14:
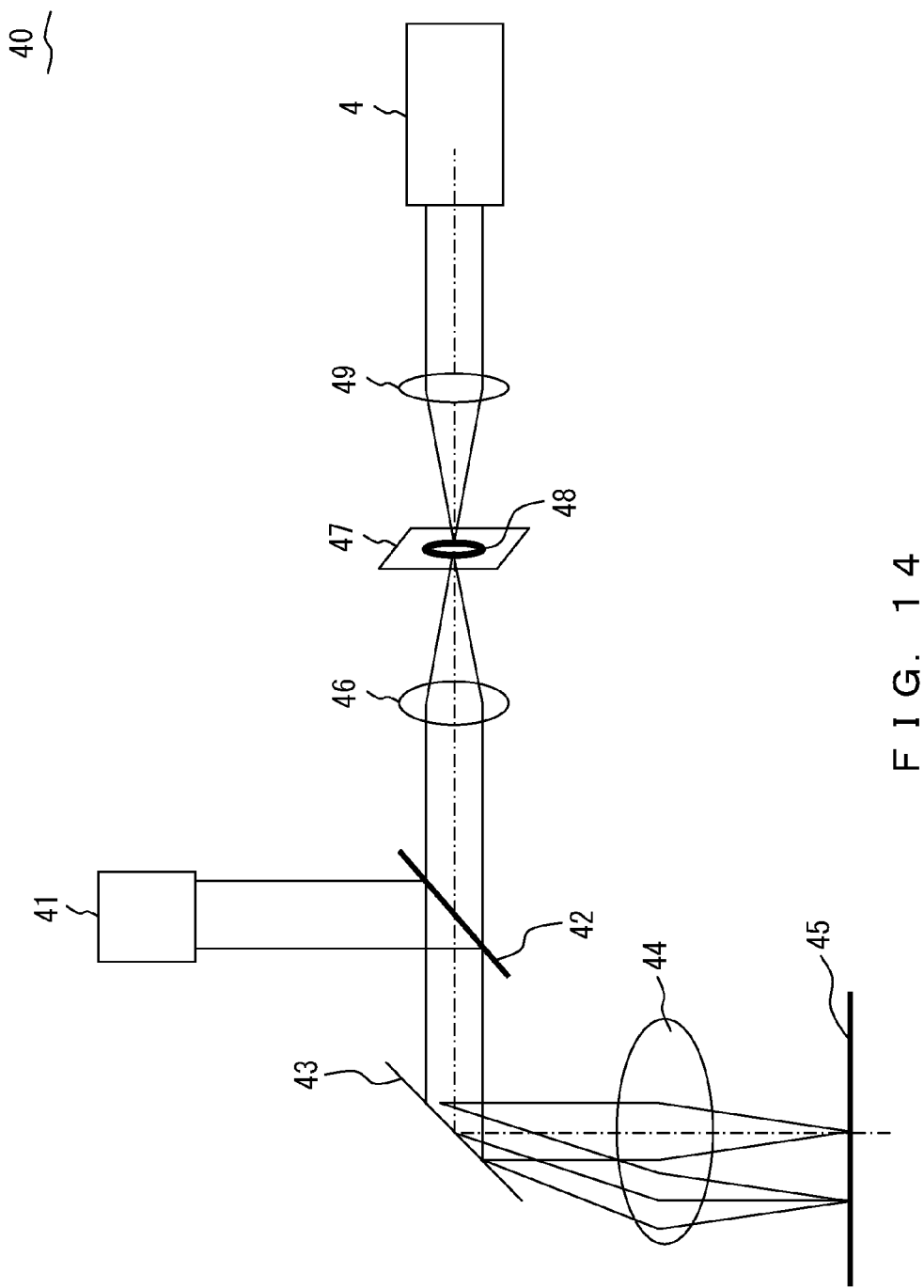
FIG. 14 is the outline of a configuration of the microscope according to the embodiment 9.

FIG. 14 is the outline of a configuration of the microscope according to the present embodiment. A microscope 40 illustrated in FIG. 14 is a confocal scanning microscope used in a fluorescent observation.

A microscope 40 includes: a laser 41; a dichroic mirror 42 which reflects a laser beam emitted from the laser 41, and passes fluorescence from a sample 45; a galvanomirror 43 for scanning the sample 45 using the laser beam; an optical scanning system 44 which irradiates the sample 45 with the laser beam; a confocal lens 46 which condenses the fluorescence that has passed through the dichroic mirror 42, a confocal stop 47 for which a confocal pin hole 48 has been formed at a position optically conjugate with the sample 45, a collimated lens 49 which collimates the fluorescence that has passed through the confocal pin hole 48; and the spectral device 4 in which the fluorescence from the collimated lens 49 enters as a parallel luminous flux.

According to the microscope 40 with the above-mentioned configuration, the spectral device 4 realizes high detection efficiency, thereby efficiently acquiring wavelength information by dispersing feeble fluorescence from the sample 45.

Although the present embodiment exemplifies the microscope 40 including the spectral device 4 according to the embodiment 1, a microscope may include a spectral device according to other embodiments.

What is claimed is:

1. A method for guiding light in a spectral device, wherein the spectral device comprises: a diffraction element which disperses light for each wavelength; an optical condensing system which condenses diffracted light of a specific order generated by diffraction in the diffraction element, the diffracted light of the specific order including first diffracted light of the specific order and second diffracted light of the specific order; a photo-detector which is arranged at a condensing position where the diffracted light of the specific order is condensed by the optical condensing system; a first deflection device which is arranged to invert a direction of travel of second light which is zeroth-order diffracted light generated by diffraction of first light which has entered the diffraction element as a parallel luminous flux, and to lead the second light into the diffraction element, whereby the second diffracted light of the specific order is generated by diffraction of the second light in the diffraction element; and a second deflection device which is arranged to invert a direction of travel of the second diffracted light of the specific order generated by the diffraction of the second light which has entered the diffraction element so as to be in a same direction as the first diffracted light of the specific order which is generated by the diffraction of the first light, and to slightly translate in parallel the second diffracted light of the specific order, so as to lead the second diffracted light of the specific order into the optical condensing system without re-entering the diffraction element;

wherein the method comprises:
diffracting, with the diffraction element, the first light which enters the diffraction element as a parallel luminous flux, to (i) generate the first diffracted light of the specific order and lead the first diffracted light to the optical condensing system to be condensed by the optical condensing system and received by the photo-detector at the condensing position, and (ii) generate the second light which is the zeroth-order diffracted light, and lead the second light to the first deflection device;
inverting, with the first deflection device, a direction of travel of the second light, to lead the second light into the diffraction element;
diffracting, with the diffraction element, the second light which entered the diffraction element, to generate the second diffracted light of the specific order, and to lead the second diffracted light of the specific order to the second deflection device;
inverting, with the second deflection device, a direction of travel of the second diffracted light of the specific order so as to be in a same direction as the first diffracted light of the specific order, and slightly translating in parallel the second diffracted light of the specific order, with the second deflection device, so as to lead the second diffracted light of the specific order into the optical condensing system without re-entering the diffraction element, wherein the second diffracted light of the specific order is condensed by the optical condensing system and received by the photo-detector at the condensing position.

2. The method according to claim 1, wherein the diffraction element is arranged as freely rotatable to change an angle of incidence of the first light.

3. The method according to claim 2, wherein the diffraction element is a transmissive diffraction grating.

4. The method according to claim 3, wherein:
the first deflection device and the second deflection device are arranged opposite each other with the diffraction element interposed between the devices; and the inverting with the first deflection device comprises inverting the direction of travel of the second light and leading the second light into the diffraction element from a surface different from a surface of incidence of the first light.

5. The method according to claim 3, wherein the diffraction element is a transmissive volume phase holographic grating.

6. The method according to claim 3, wherein the second deflection device comprises:
a second optical condensing system having a front focal position at a position where the first light enters the diffraction element; and
a reflective member arranged at a back focal position of the second optical condensing system,
wherein the inverting with the second deflection device comprises:
condensing, with the second optical condensing system, the second diffracted light of the specific order to thereby lead the second diffracted light to the reflective member; and
reflecting, with the reflective member, the second diffracted light of the specific order.

7. The method according to claim 2, wherein the diffraction element is a reflective diffraction grating.

8. The method according to claim 7, wherein the second deflection device comprises:
an inversion member which is arranged to invert the direction of travel of the second diffracted light of the specific order generated by diffraction of the second light; and
a reflective member which is arranged to reflect the second diffracted light of the specific order whose direction of travel is inverted by the inversion member, the reflective member being arranged near the diffraction element;
wherein the inverting with the second deflection device comprises:
inverting, with the inversion member, the direction of travel of the second diffracted light of the specific order to lead the second diffracted light of the specific order to the reflective member; and
reflecting, with the reflective member, the second diffracted light of the specific order.

9. The method according to claim 7, wherein the second deflection device comprises:
a second optical condensing system having a front focal position at a position where the first light enters the diffraction element;
a first reflective member arranged at a back focal position of the second optical condensing system; and
a second reflective member which is arranged to reflect the second diffracted light of the specific order whose direction of travel has been inverted by the second optical condensing system and the reflective member, the second reflective member being arranged near the diffraction element,
wherein the inverting with the second deflection device comprises:
condensing, with the second optical condensing system, the second diffracted light of the specific order to thereby lead the second diffracted light to the first reflective member;
reflecting, with the first reflective member, the second diffracted light to lead the second refractive light to the second optical condensing system;
condensing the second diffracted light with the second optical condensing system to thereby lead the second diffracted light to the second reflective member; and
reflecting, with the second reflective member, the second diffracted light.

10. The method according to claim 7, wherein:
the first deflection device is a reflective member which is arranged to rotate with a rotation of the diffraction element, and to travel by rotating about a rotation axis of the diffraction element two times a rotation angle of the diffraction element, and
the second deflection device is arranged to rotate with a rotation of the diffraction element, and to travel by rotating about the rotation axis of the diffraction element at a same rotation angle as the diffraction element.

11. The method according to claim 1, further comprising a third deflection device which is arranged to invert a direction of travel of third light which is zeroth-order diffracted light generated by diffraction of the second light, and to lead the third light into the diffraction element,
wherein the method further comprises inverting, with the third deflection device, the direction of travel of the third light, to lead the third light into the diffraction element.

12. The method according to claim 1, wherein the photodetector comprises a plurality of detection elements which detect diffracted light of the specific order having different wavelength bands.

13. The method according to claim 1, wherein the second deflection device comprises a corner cube, and the inverting with the second deflection device comprises inverting the direction of travel of the second diffracted light and slightly translating in parallel the second diffracted light with the corner cube.

* * * * *